United States Patent
Yu et al.

(10) Patent No.: US 11,182,898 B2
(45) Date of Patent: Nov. 23, 2021

(54) SYSTEM AND METHOD FOR IMAGE RECONSTRUCTION

(71) Applicant: UIH AMERICA, INC., Houston, TX (US)

(72) Inventors: Zhicong Yu, Houston, TX (US); Stanislav Zabic, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 0 days.

(21) Appl. No.: 16/786,438

(22) Filed: Feb. 10, 2020

(65) Prior Publication Data

US 2020/0175682 A1    Jun. 4, 2020

Related U.S. Application Data

(63) Continuation of application No. 15/599,569, filed on May 19, 2017, now Pat. No. 10,559,079.

(51) Int. Cl.
| | | |
|---|---|---|
| G06K 9/00 | (2006.01) |
| G06T 7/00 | (2017.01) |
| G06T 11/00 | (2006.01) |
| A61B 6/03 | (2006.01) |
| A61B 6/00 | (2006.01) |

(52) U.S. Cl.
CPC .......... *G06T 7/0012* (2013.01); *A61B 6/032* (2013.01); *A61B 6/5205* (2013.01); *G06T 11/003* (2013.01); *G06T 11/005* (2013.01); *G06T 11/006* (2013.01); *G06T 11/008* (2013.01); *G06T 2207/10081* (2013.01); *G06T 2211/424* (2013.01)

(58) Field of Classification Search
None
See application file for complete search history.

(56) References Cited

U.S. PATENT DOCUMENTS

| | | |
|---|---|---|
| 6,608,942 B1 | 8/2003 | Le |
| 2010/0054622 A1 | 3/2010 | Adams |
| 2011/0044524 A1 | 2/2011 | Wang et al. |
| 2014/0201126 A1 | 7/2014 | Zadeh et al. |
| 2015/0093015 A1 | 4/2015 | Liang et al. |
| 2016/0140725 A1 | 5/2016 | Bergner et al. |

(Continued)

FOREIGN PATENT DOCUMENTS

| | | |
|---|---|---|
| CN | 106204445 A | 12/2016 |
| WO | 2011023969 A1 | 3/2011 |
| WO | 2014177953 A1 | 11/2014 |

OTHER PUBLICATIONS

Joachim Weickert, Anisotropic Diffusion in Image Processing, B.g.teubner Stuttgart, 1996, 173 pages.

(Continued)

*Primary Examiner* — Wei Wen Yang
(74) *Attorney, Agent, or Firm* — Metis IP LLC

(57) ABSTRACT

The present disclosure relates to systems and methods for image reconstruction. The systems may perform the methods to obtain image data, at least a portion of the image data relating to a region of interest (ROI); determine local information of the image data, the local information relating to orientation information of the image data; determine a regularization item based on the local information; and modify the image data based on the regularization item.

20 Claims, 12 Drawing Sheets

(56) References Cited

U.S. PATENT DOCUMENTS

2016/0225169 A1 8/2016 Bippus et al.
2017/0193692 A1* 7/2017 Huang .................. G06T 7/20

OTHER PUBLICATIONS

Antoni Buades et al., A Non-local Algorithm for Image Denoising, IEEE Computer Society Conference on Computer Vision and Pattern Recognition, 2005, 6 pages.

C. Tomasi et al., Bilateral Filtering for Gray and Color Images, IEEE International Conference on Computer Vision, 1998, 8 pages.

Markus Grasmair et al, Anisotropic Total Variation Filtering, Applied Mathematics & Optimization, 62: 323-339, 2010.

Virginia Estellers et al., Adaptive Regularization With the Structure Tensor, IEEE Transactions on Image Processing, 24(6): 1777-1790, 2015.

Zhicong Yu et al., Coherent L1 Norm Regularization for Edge Correction in Low-dose Iterative Image Reconstruction, the 14th International Meeting on Fully Three-Dimensional Image Reconstruction in Radiology and Nuclear Medicine, 743-746, 2017.

European Search Report in European Application No. 17178732.8 dated Dec. 19, 2017, 7 pages.

Yan Honghai et al., Video Super Resolution Method Based on Structure Tensor, Journal of Computer Applications, 36(7), 6 pages, 2016.

Wang Yiyan, Medical Image Restoration Via Joint Structure Tensor and Variable Index Regularization Variational, Computer Engineering and Applications, 52(15): 208-211, 2016.

First Office Action in Chinese Application No. 201710521098.9 dated Oct. 26, 2020, 16 pages.

Liu, Shu, Post-processing Technology of Surveillance Image/Video, China Excellent Master's Thesis Full-text Database Information Technology Series, 2015, 73 pages.

* cited by examiner

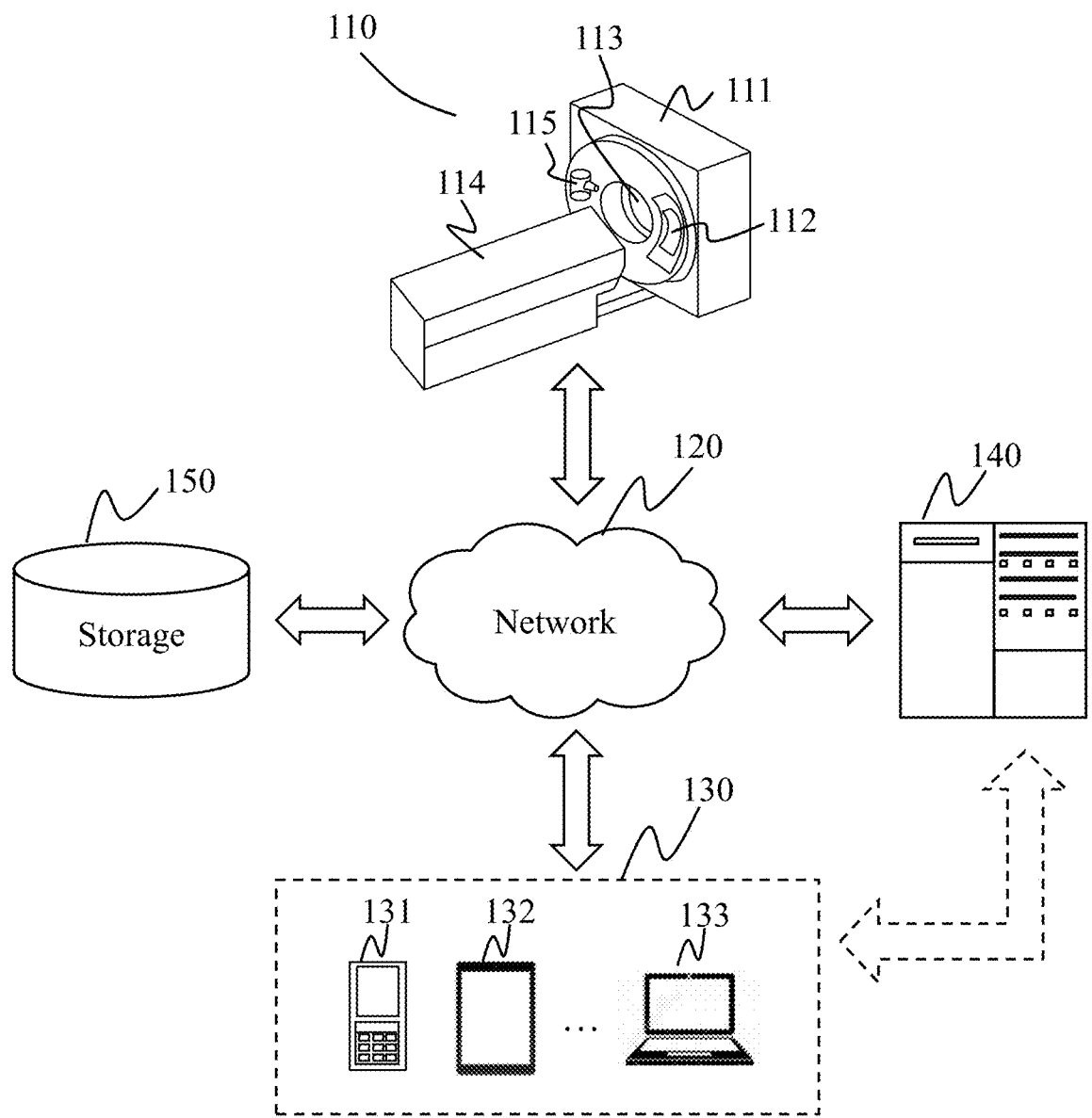
FIG. 1-A

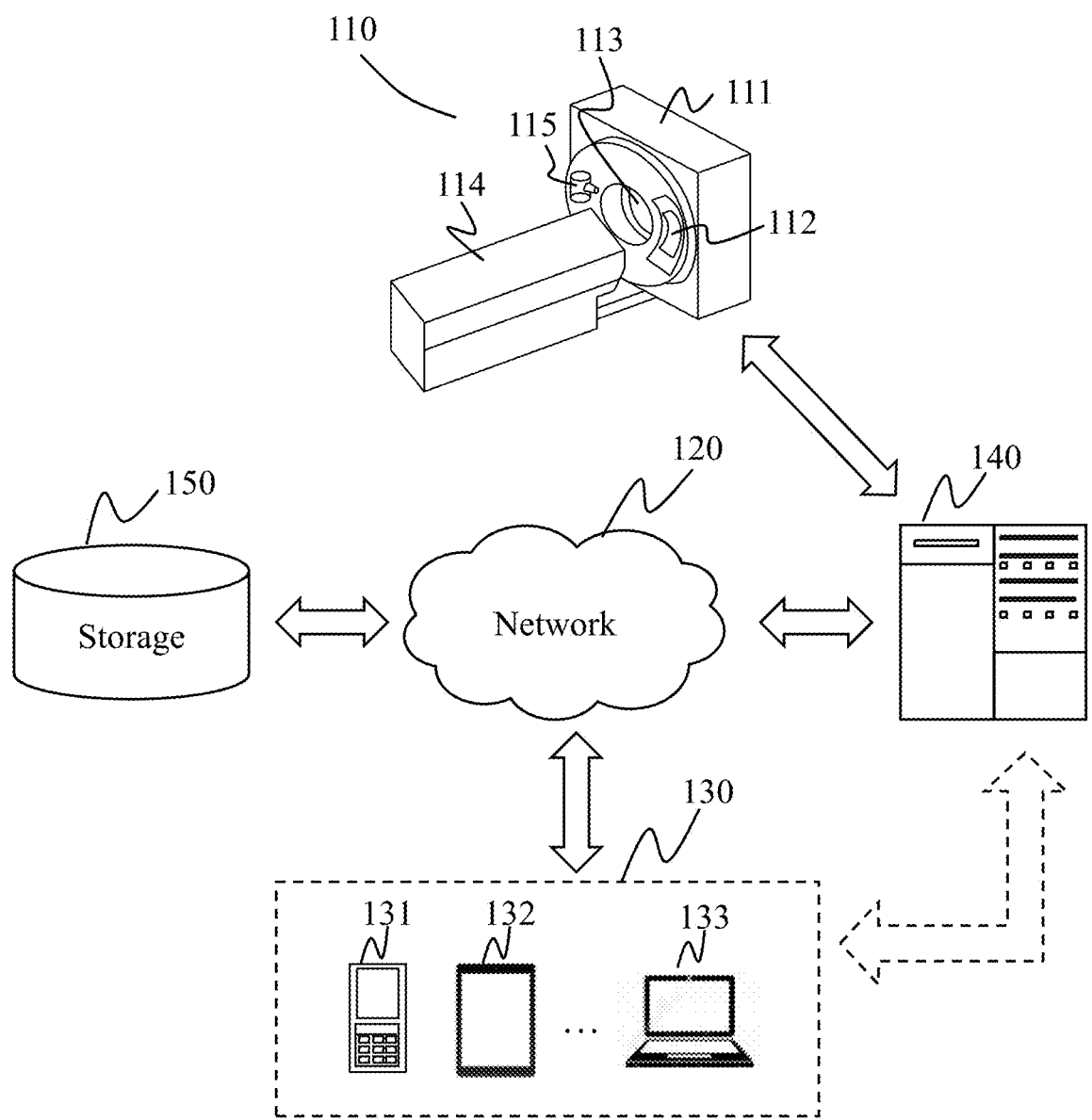
FIG. 1-B

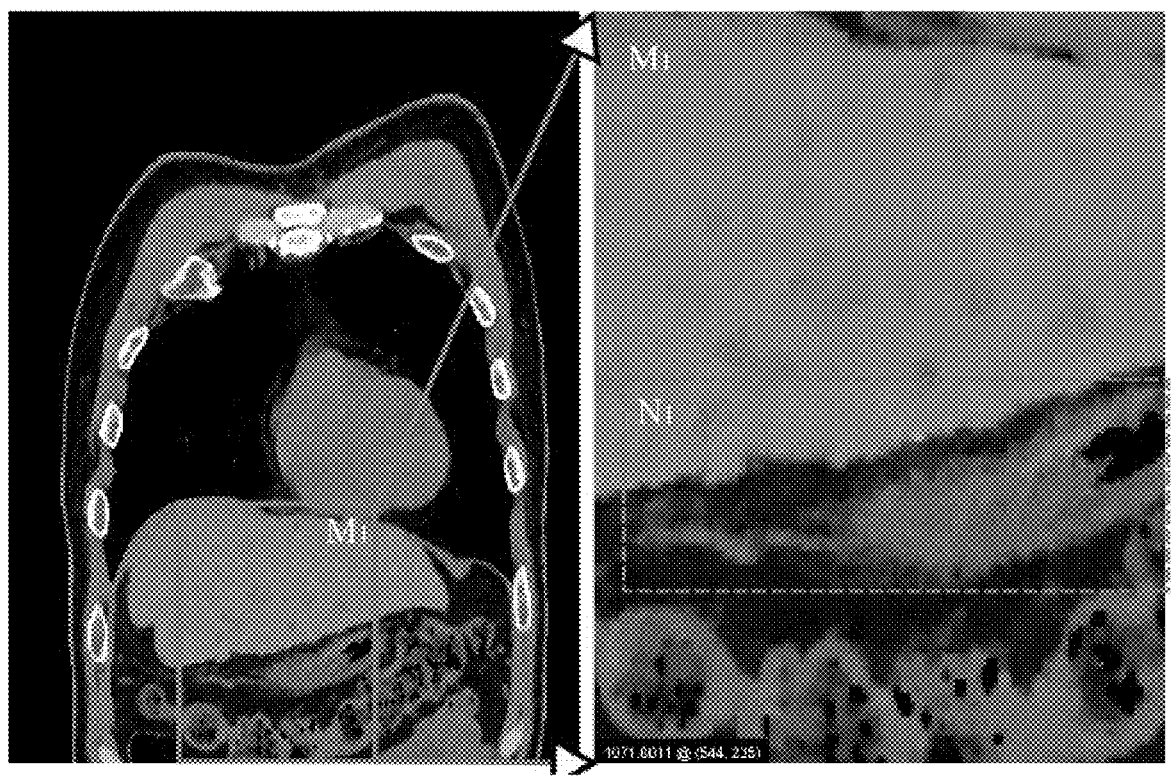
FIG. 11-A
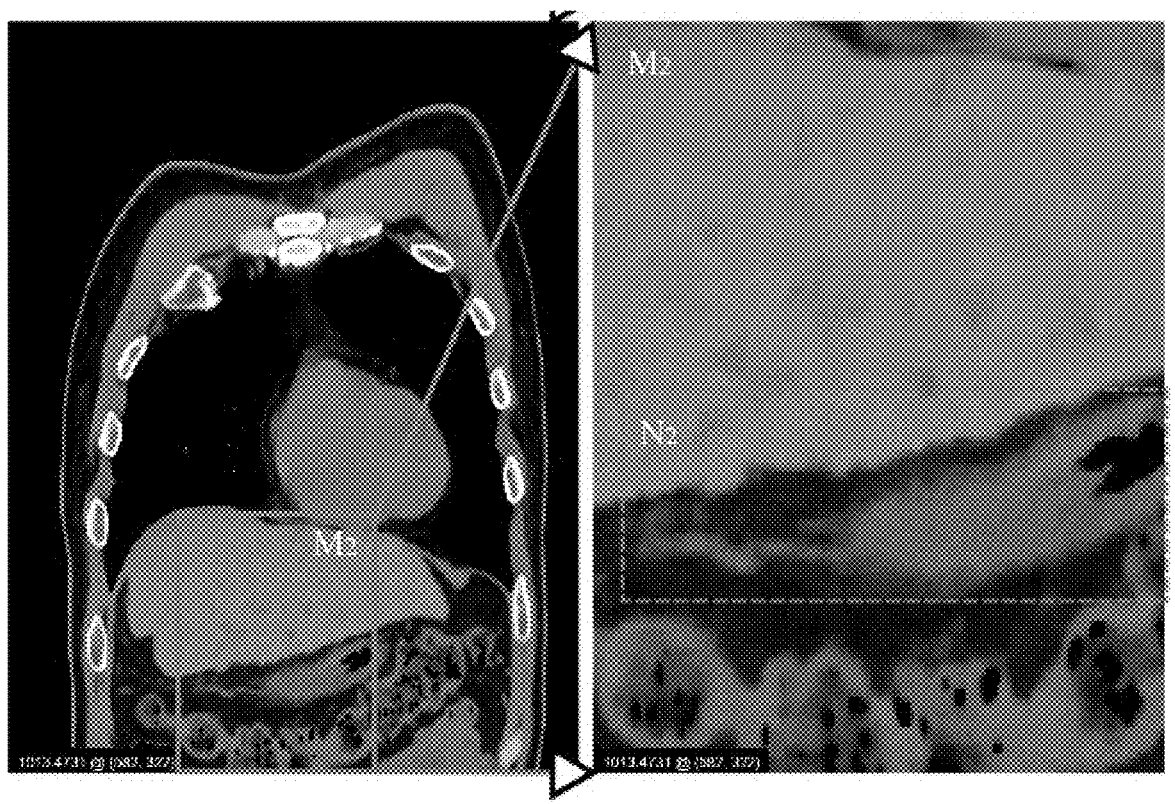
FIG. 11-B

SYSTEM AND METHOD FOR IMAGE RECONSTRUCTION

CROSS-REFERENCE TO RELATED APPLICATIONS

This application is a continuation of U.S. application Ser. No. 15/599,569, filed on May 19, 2017, the entire contents of each of which are hereby incorporated by reference.

TECHNICAL FIELD

The present disclosure generally relates to image reconstruction, and more specifically relates to methods and systems for iterative image reconstruction.

BACKGROUND

Computed tomography (CT) is a technology that makes use of computer-processed combinations of X-ray projections taken from different angles to produce cross-sectional images. The CT technology has been widely used in medical diagnosis. During a reconstruction process of a CT image, artifacts (e.g., staircase artifacts) may appear on tissue boundaries. The artifacts may reduce the image quality and influence the results of diagnosis on the basis of such an image. It is desirable to provide systems and methods for reconstructing a CT image with improved quality and reduced artifacts.

SUMMARY

In a first aspect of the present disclosure, a method for image reconstruction is provided. The method may include one or more of the following operations. Image data may be obtained. At least a portion of the image data may be relating to a region of interest (ROI). Local information of the image data may be determined. The local information may be relating to orientation information of the image data. A regularization item may be determined based on the local information. The image data may be modified based on the regularization item. An image maybe generated based on the modified image data.

In some embodiments, gradient information of the image data may be determined. The image data may be smoothed. Orientation information of the smoothed image data may be determined. The regularization item may be determined based on the gradient information of the image data and the orientation information of the smoothed image data.

In some embodiments, the image data may be smoothed based on a first low-pass filter.

In some embodiments, the orientation information may include a structure tensor of the smoothed image data or a modified structure tensor of the smoothed image data.

In some embodiments, the structure tensor of the smoothed image data may be determined. The structure tensor may be smoothed. Eigenvalues of the smoothed structure tensor may be determined. The Eigenvalues may be modified. A modified structure tensor may be determined based on the modified Eigenvalue.

In some embodiments, an Eigenvalue adjustment function may be determined based on at least a portion of the image data relating to the ROI. The Eigenvalues may be revised based on the Eigenvalue adjustment function.

In some embodiments, the ROI may include a region relating to a liver, a bone, or a kidney.

In some embodiments, a first-order differentiation of the smoothed image data may be determined. A transpose of the first-order differentiation of the smoothed image data may be determined. The structure tensor of the smoothed image data may be determined based on the first-order differentiation of the smoothed image data and the transpose of the first-order differentiation of the smoothed image data.

In some embodiments, a second low-pass filter may be applied on the structure tensor.

In some embodiments, the gradient information may be determined based on a first-order differentiation of the image data.

In some embodiments, projection data may be obtained. The image data may be generated based on the projection data.

In some embodiments, the image data may be updated based on an iterative statistical reconstruction algorithm.

In some embodiments, the image data may include a 2D image, 2D image data, a 3D image, or 3D image data.

In a second aspect of the present disclosure, a method for image reconstruction is provided. The method may include one or more of the following operations. Image data may be obtained. At least a portion of the image data may be relating to a region of interest (ROI). Gradient information of the image data may be determined. The image data may be smoothed. A structure tensor of the smoothed image data may be determined. The structure tensor may be smoothed. Eigenvalues of the smoothed structure tensor may be determined. The Eigenvalues may be modified. A modified structure tensor may be determined based on the modified Eigenvalues. A regularization item may be determined based on the gradient information and the modified structure tensor. The image data may be modified based on the regularization item. An image may be generated based on the modified image data.

In some embodiments, an Eigenvalue adjustment function may be determined based on the at least a portion of the image data relating to the ROI. The Eigenvalues may be revised based on the Eigenvalue adjustment function.

In some embodiments, the ROI may include a region relating to a liver, a bone, or a kidney.

In a third aspect of the present disclosure, a system is provided. The system may include at least one storage medium and at least one processor. The at least one storage medium may include a set of instructions for image reconstruction. The set of instructions, when executed by the at least one processor, may cause the system to perform one or more of the following operations. The system may obtain image data, wherein at least a portion of the image data may relate to a region of interest (ROI). The system may determine local information of the image data, wherein the local information may relate to orientation information of the image data. The system may determine a regularization item based on the local information. The system may modify the image data based on the regularization item. The system may generate an image based on the modified image data.

In some embodiments, the system may determine gradient information of the image data. The system may smooth the image data. The system may determine orientation information of the smoothed image data. The system may determine the regularization item based on the gradient information of the image data and the orientation information of the smoothed image data.

In some embodiments, the system may determine the structure tensor of the smoothed image data. The system may smooth the structure tensor. The system may determine Eigenvalues of the smoothed structure tensor. The system may modify the Eigenvalues. The system may determine a modified structure tensor based on the modified Eigenvalues.

In some embodiments, the system may determine an Eigenvalue adjustment function based on at least a portion of the image data relating to the ROI. The system may revise the Eigenvalues based on the Eigenvalue adjustment function.

In some embodiments, the system may determine a first-order differentiation of the smoothed image data. The system may determine a transpose of the first-order differentiation of the smoothed image data. The system may determine the structure tensor of the smoothed image data based on the first-order differentiation of the smoothed image data and the transpose of the first-order differentiation of the smoothed image data.

In some embodiments, the system may obtain projection data. The system may generate the image data based on the projection data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A and FIG. 1-B are schematic diagrams illustrating an exemplary CT system according to some embodiments of the present disclosure;

FIG. 11-A and FIG. 11-B illustrate exemplary CT images reconstructed based on different reconstruction approaches according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
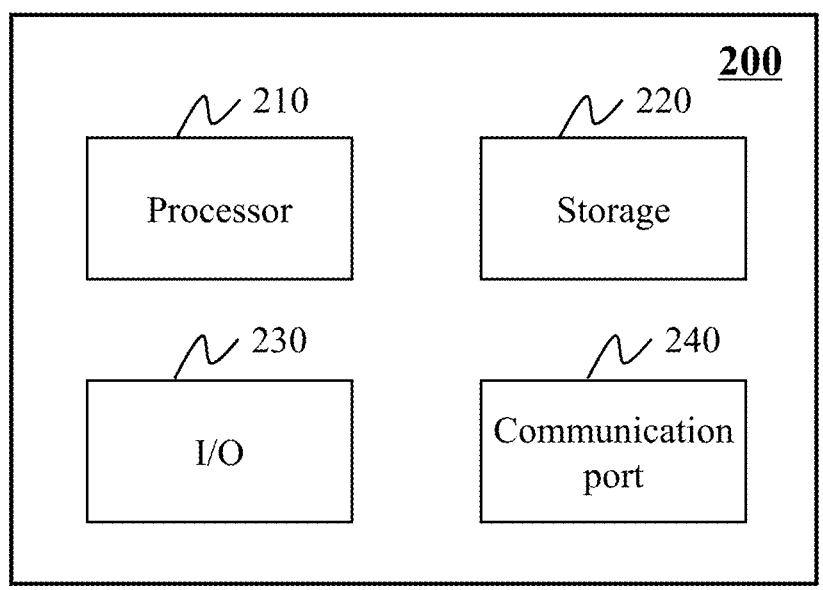
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, an emission computed tomography (ECT) system, a magnetic resonance imaging (MM) system, an ultrasonography system, a positron emission tomography (PET) system, or the like, or any combination thereof.

The method and system disclosure herein may be applied for reconstruction of other types of images including, for example, CT images, ECT images, magnetic resonance (MR) images, PET images, etc. For illustration purposes and not intended to limit the scope of the present disclosure, the disclosure is provided in connection with CT image reconstruction. The system may reconstruct a CT image based on a statistical image reconstruction algorithm. The statistical image reconstruction algorithm may include a regularization item that may be used to reduce staircase artifacts during the statistical image reconstruction.

The following description is provided to help better understanding CT image reconstruction methods and/or systems. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

FIGS. 1-A and 1-B are schematic diagrams illustrating an exemplary CT system 100 according to some embodiments of the present disclosure. As shown, the CT system 100 may include a CT scanner 110, a network 120, one or more terminals 130, a processing engine 140, and a storage 150.

The CT scanner 110 may include a gantry 111, a detector 112, a detecting region 113, a table 114, and a radioactive scanning source 115. The gantry 111 may support the detector 112 and the radioactive scanning source 115. A subject may be placed on the table 114 for scanning. The radioactive scanning source 115 may emit radioactive rays to the subject. The detector 112 may detect radiation events (e.g., gamma photons) emitted from the detecting region 113. In some embodiments, the detector 112 may include one or more detector units. The detector units may include a scintillation detector (e.g., a cesium iodide detector), a gas detector, etc. The detector unit may be and/or include a single-row detector and/or a multi-rows detector.

The network 120 may include any suitable network that can facilitate exchange of information and/or data for the CT system 100. In some embodiments, one or more components of the CT system 100 (e.g., the CT scanner 110, the terminal 130, the processing engine 140, the storage 150, etc.) may communicate information and/or data with one or more other components of the CT system 100 via the network 120. For example, the processing engine 140 may obtain image data from the CT scanner 110 via the network 120. As another example, the processing engine 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the CT system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift', a Hololens™, a Gear VR™, etc. In some embodiments, the terminal(s) 130 may be part of the processing engine 140.

The processing engine 140 may process data and/or information obtained from the CT scanner 110, the terminal 130, and/or the storage 150. For example, the processing engine 140 may process image data and determine a regularization item that may be used to modify the image data. In some embodiments, the processing engine 140 may be a single server or a server group. The server group may be centralized or distributed. In some embodiments, the processing engine 140 may be local or remote. For example, the processing engine 140 may access information and/or data stored in the CT scanner 110, the terminal 130, and/or the storage 150 via the network 120. As another example, the processing engine 140 may be directly connected to the CT scanner 110, the terminal 130 and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The storage 150 may store data, instructions, and/or any other information. In some embodiments, the storage 150 may store data obtained from the terminal 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the CT system 100 (e.g., the processing engine 140, the terminal 130, etc.). One or more components in the CT system 100 may access the data or instructions stored in the storage 150 via the network 120. In some embodiments, the storage 150 may be directly connected to or communicate with one or more other components in the CT system 100 (e.g., the processing engine 140, the terminal 130, etc.). In some embodiments, the storage 150 may be part of the processing engine 140.

FIG. 2 is a schematic diagram illustrating exemplary hardware and/or software components of an exemplary computing device 200 on which the processing engine 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 140 in accordance with techniques described herein. The computer instructions may include, for example, routines, programs, objects, components, data structures, procedures, modules, and functions, which perform particular functions described herein. For example, the processor 210 may process image data obtained from the CT scanner 110, the terminal 130, the storage 150, and/or any other component of the CT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the CT scanner 110, the terminal 130, the storage 150, and/or any other component of the CT system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 140 for determining a regularization item.

The I/O 230 may input and/or output signals, data, information, etc. In some embodiments, the I/O 230 may enable a user interaction with the processing engine 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing engine 140 and the CT scanner 110, the terminal 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
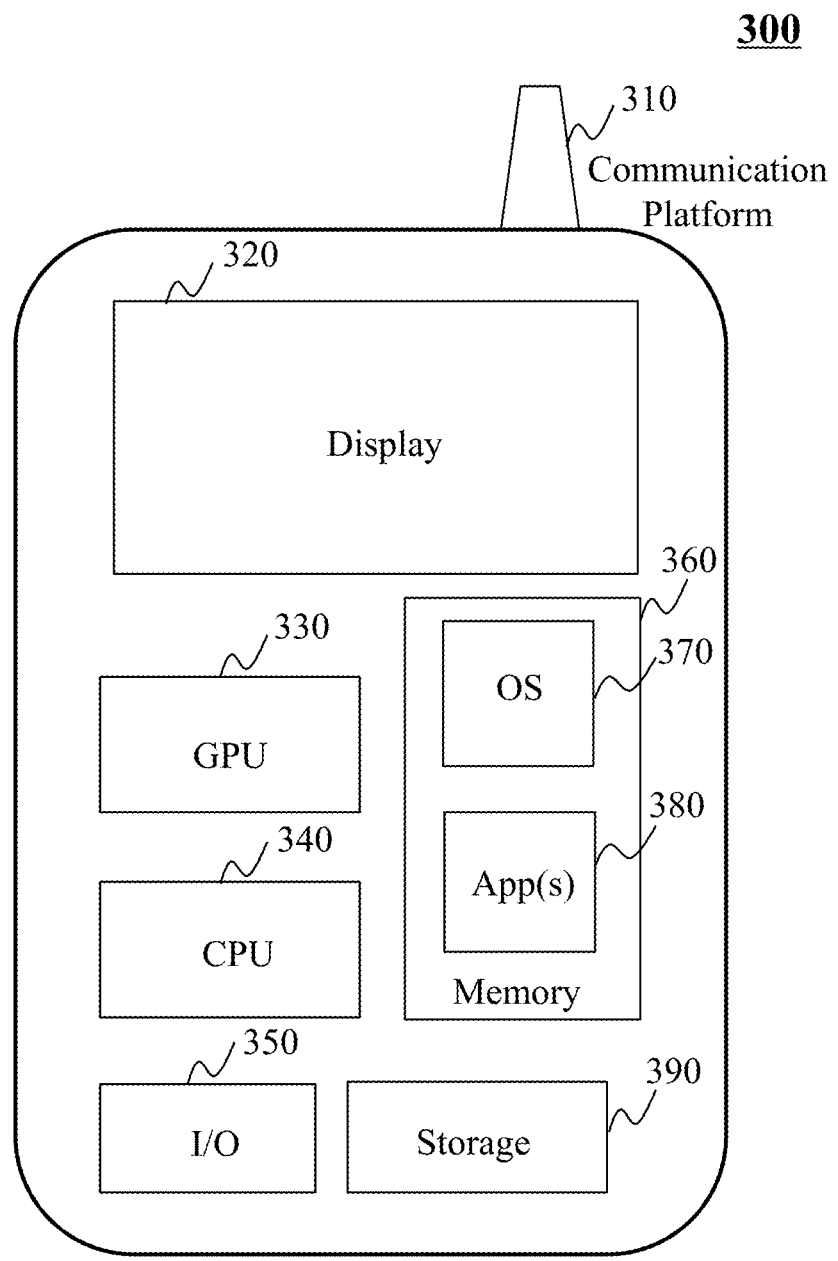
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android", Windows Phone", etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 140. User interactions with the information stream may be achieved via the I/O 350 and provided to the processing engine 140 and/or other components of the CT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
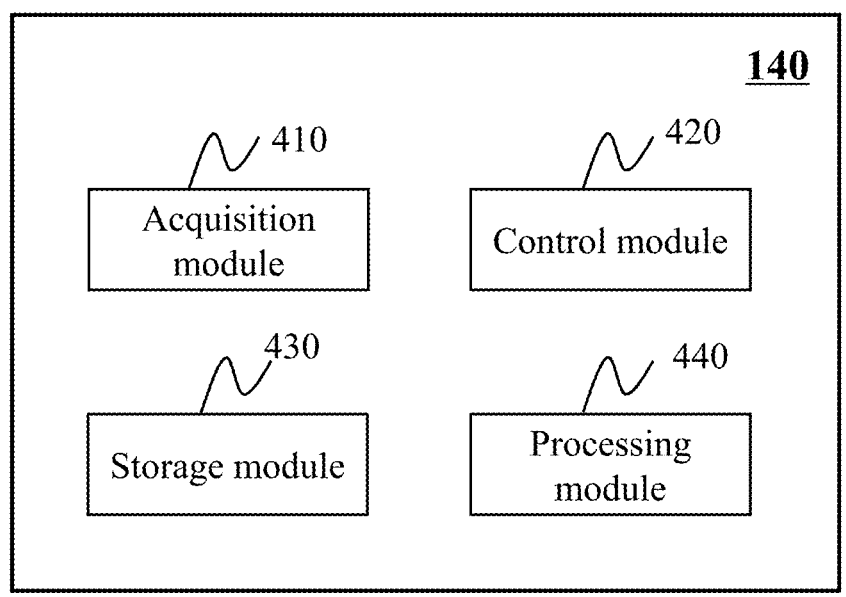
FIG. 4 is a block diagram illustrating an exemplary processing engine according to some embodiments of the present disclosure.

FIG. 4 is a block diagram illustrating an exemplary processing engine 140 according to some embodiments of the present disclosure. The processing engine 140 may include an acquisition module 410, a control module 420, a storage module 430, and a processing module 440.

The acquisition module 410 may acquire CT data. The acquisition module 410 may acquire the CT data from the detector 112. The CT data may be associated with X-rays that pass through a subject. In some embodiments, the radioactive scanning source 115 may emit the X-rays to the subject. The X-rays may pass through the subject and may attenuate during the passing process. The attenuated X-rays may be detected by the detector 112 and transmitted to the acquisition module 410. In some embodiments, the acquired CT data may be transmitted to the storage module 430 to be stored.

The control module 420 may control operations of the acquisition module 410, the storage module 430, and/or the processing module 440 (e.g., by generating one or more control parameters). For example, the control module 420 may control the acquisition module 410 to acquire a signal, the timing of the acquisition of the signal, etc. As another example, the control module 420 may control the processing module 440 to process the CT data acquired by the acquisition module 410. In some embodiments, the control module 420 may receive a real-time command or retrieve a predetermined command provided by a user (e.g., a doctor) to control one or more operations of the acquisition module 410 and/or the processing module 440. For example, the control module 420 can adjust the acquisition module 410 and/or the processing module 440 to generate images of a subject according to the real-time command and/or the predetermined command. In some embodiments, the control module 420 may communicate with one or more other modules of the processing engine 140 for exchanging information and/or data.

The storage module 430 may store CT data, control parameters, processed CT data, or the like, or a combination thereof. In some embodiments, the storage 430 may store one or more programs and/or instructions that may be executed by the processor(s) of the processing engine 140 to perform exemplary methods described in this disclosure. For example, the storage 430 may store program(s) and/or instruction(s) that can be executed by the processor(s) of the processing engine 140 to acquire CT data, reconstruct a CT image based on the CT data, and/or display any intermediate result or a resultant image.

The processing module 440 may process information provided by various modules of the processing engine 140. The processing module 440 may process CT data acquired by the acquisition module 410, CT data retrieved from the storage module 430, etc. In some embodiments, the processing module 440 may reconstruct CT images based on the CT data according to a reconstruction algorithm, generate reports including one or more CT images and/or other related information, and/or perform any other function for image reconstruction in accordance with various embodiments of the present disclosure. The reconstruction algorithm may include an iterative reconstruction algorithm (e.g., a statistical reconstruction algorithm), an analytic reconstruction algorithm, or the like, or any combination thereof. For example, the processing module 440 may determine a regularization item for the CT data and reconstruct a CT image based on the regularization item.

In some embodiments, one or more modules illustrated in FIG. 4 may be implemented in at least part of the exemplary CT system as illustrated in FIGS. 1-A and 1-B. For example, the acquisition module 410, the control module 420, the storage module 430, and/or the processing module 440 may be integrated into a console (not shown). Via the console, a user may set parameters for scanning an object, controlling imaging processes, controlling parameters for reconstruction of an image, viewing reconstructed images, etc. In some embodiments, the console may be implemented via the processing engine 140 and/or the terminal 130.

Figure 5:
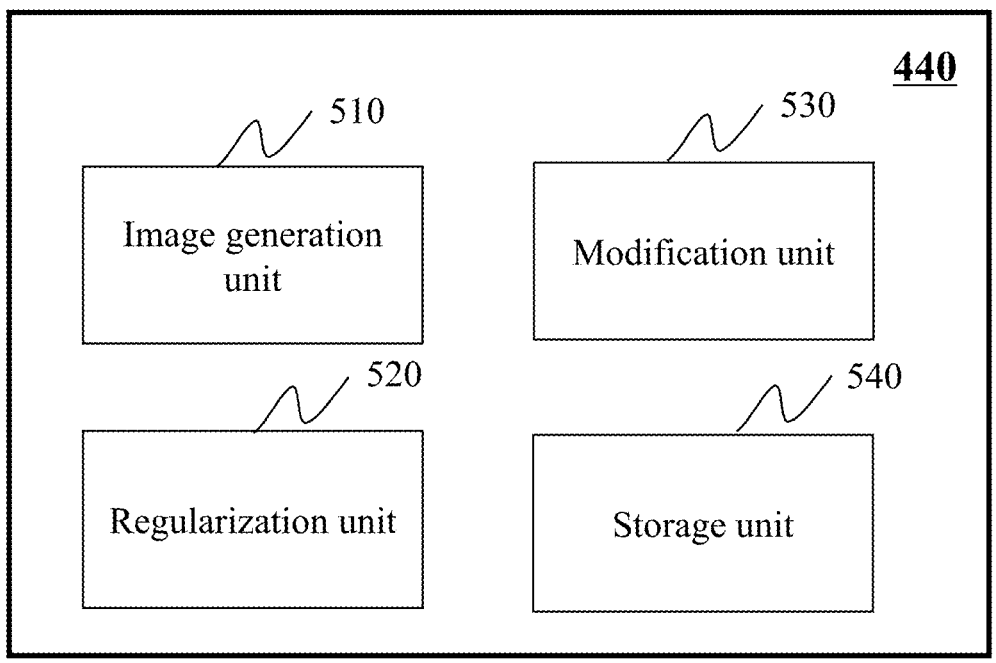
FIG. 5 is a block diagram illustrating an exemplary processing module according to some embodiments of the present disclosure.

FIG. 5 is a block diagram illustrating an exemplary processing module 440 according to some embodiments of the present disclosure. The processing module 440 may include an image generation unit 510, a regularization unit 520, a modification unit 530, and a storage unit 540. The processing module 440 may be implemented on various components (e.g., the processor 210 of the computing device 200 as illustrated in FIG. 2).

The image generation unit 510 may obtain or update original image data (also referred to as an "original image"). The image data may include 2D image data, a 2D image, 3D image data, a 3D image, 4D image data, a 4D image, or the like, or any combination thereof. For example, the image data may be 3D CT image data or a 3D CT image. The original image data may be further processed by the regularization unit 520 and/or the modification unit 530, or may be stored in the storage unit 540 or any storage device disclosed elsewhere in the present disclosure.

The regularization unit 520 may determine a regularization item. As used herein, the regularization item may refer to an item that may be used to regularize the original image data during an image reconstruction process. For example, during an image reconstruction process, a surface of a tissue in the image may be smoothed based on the regularization item. In some embodiments, the regularization unit 520 may determine the regularization item based on a total variation (TV) of the original image data. In some embodiments, the regularization unit 520 may further determine a regularization parameter. As used herein, the regularization parameter may refer to a parameter that may be used to control a strength of the regularization item. In some embodiments, the regularization parameter may be provided as part of default settings (e.g., a constant) of the CT system 100. In some embodiments, the regularization parameter may be adjusted in different situations. Merely by way of example, a default value or a reference value of the regularization parameter may be provided by the processing engine 140, and adjusted based on a specific situation in which the regularization parameter is used.

The modification unit 530 may modify the original image data based on the regularization item. In some embodiments, the modification unit 530 may further provide a user interface (not shown). For instance, the user interface may be implanted on the terminal 130. A user (e.g., a doctor) may input one or more parameters to adjust the original image via the user interface. For example, the user may enlarge or shrink the original image. As another example, the user may modify a contrast of the original image.

The storage unit 540 may store the original image data, the regularization item, the modified image data, or the like. In some embodiments, the storage format may include text, picture, audio, video, code, or the like, or a combination thereof. In some embodiments, one or more algorithms that may be used when, for example, the original image data are obtained or updated, the regularization item is determined, etc., may be stored in the storage unit 540.

It should be noted that the above description of the processing module is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more units in the processing module 440 may include an independent storage block (not shown) respectively. As another example, any two or more units may be combined as an independent unit used to implement more than one functions. As a further example, the storage unit 540 may be unnecessary and the processing module 440 may share the storage module 430 with the processing engine 140. As still a further example, any one of the units may be divided into two or more sub-units.

Figure 6:
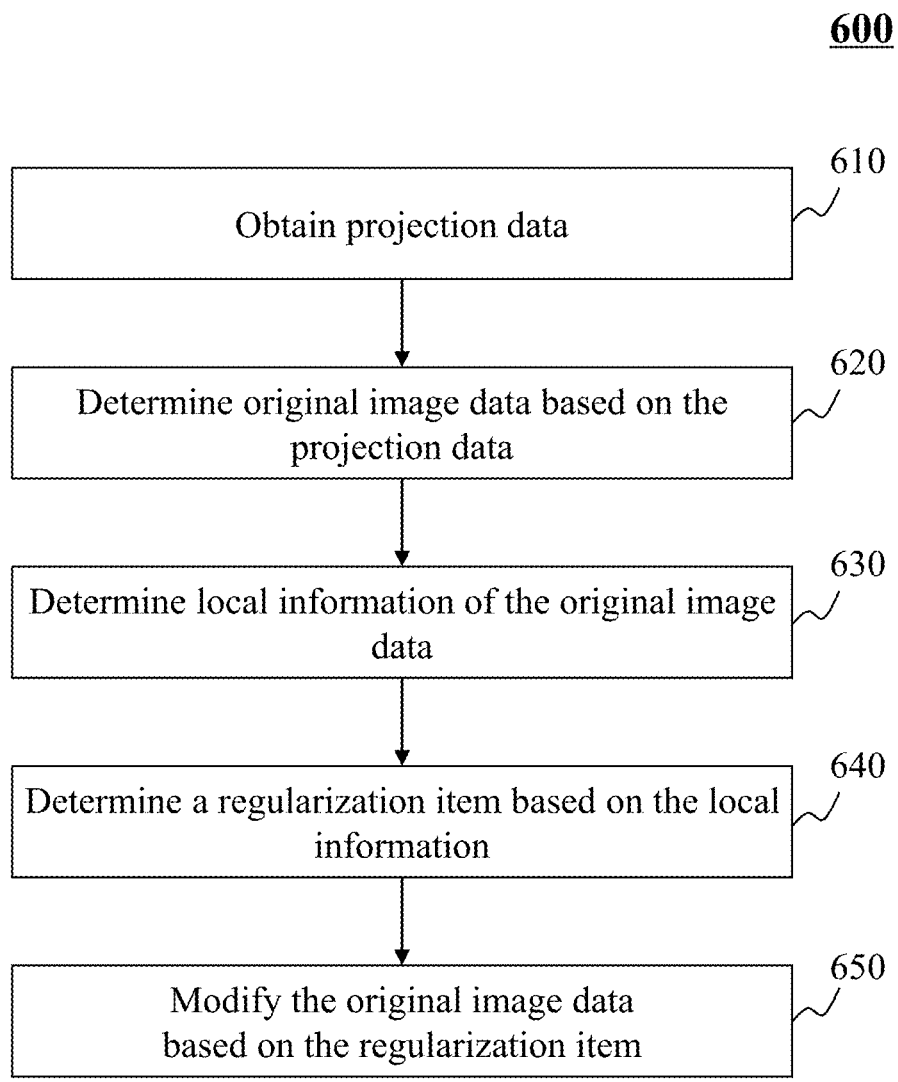
FIG. 6 is a flowchart illustrating an exemplary process for reconstructing image data according to some embodiments of the present disclosure.

FIG. 6 is a flowchart illustrating an exemplary process 600 for reconstructing image data according to some embodiments of the present disclosure.

In 610, projection data (also referred to as "measured projection data") may be obtained. The projection data may be obtained by the image generation unit 510. As used herein, the projection data may refer to two-dimensional data corresponding to an image or image data that is projected onto a specific projection plane. For example, the projection data may be determined based on a projection matrix. The projection matrix may be part of default settings of the processing engine 140, or may be adjusted by a user (e.g., a doctor). In some embodiments, the projection data may be determined based on the CT data acquired by the acquisition module 410. In some embodiments, the projection data may be processed. For example, the projection data may be filtered according to a low-pass filter (e.g., a Gaussian filter) in order to remove or reduce noise(s) in the projection data.

In 620, original image data may be determined based on the projection data. The original image data may be determined by the image generation unit 510. In some embodiments, the original image data may be generated based on the projection data according to one or more reconstruction algorithms. In some embodiments, the original image data may be determined based on default settings of the processing engine 140. For example, the original image data may be an image of which voxel values or pixel values (e.g., grey values) are all zeros. As another example, the original image data may be a mould image relating to a mould (e.g., a liver mould). In some embodiments, the original image data may be provided by a user (e.g., a doctor).

In 630, local information of the original image data may be determined. The local information of the original image data may be determined by the regularization unit 520. As used herein, the local information may refer to information that may indicate one or more features of the original image data (e.g., gradient information).

In 640, a regularization item may be determined based on the local information of the original image data. The regularization item may be determined by the regularization unit 520. As used herein, the regularization item may refer to an item that may be used to regularize the original image data during an image reconstruction process. In some embodiments, the regularization item may include a total-variationbased (TV based) regularization item, a Tikhonov regularization item, a bilateral total variation regularization item, a local information adaptive total variation regularization item, or the like, or any combination thereof. In some embodiments, a regularization parameter may be further determined. As used herein, the regularization parameter may refer to a parameter that may be used to control a strength of the regularization item.

In 650, the original image data may be modified based on the regularization item. The original image data may be modified by the modification unit 530. In some embodiments, the regularization parameter may be also taken into consideration in the modification of the original image data.

In some embodiments, the process 600 may be an iterative process or a cyclic process. After the original image data is modified based on the regularization item and/or the regularization parameter to provide the modified image data. The intermediate projection data (e.g., forward projection data) of the modified image data may be obtained and compared with the measured projection data, if a difference between the intermediate projection data and the measured projection data exceeds a threshold, the original image data may be updated and the process 600 may return to 620 to start a new iteration (i.e., a second iteration) until the difference is less than the threshold. The threshold used herein may be part of default settings of the processing engine 140, or may be adjusted by a user (e.g., a doctor). As used herein, in an ith iteration, image data may be referred to as "ith intermediate image data," corresponding projection data may be referred to as "ith intermediate projection data". In this disclosure, the original image data and the intermediate image data may be collectively referred to as "image data" or "image." Merely by way of example, the process 600 may be expressed as formula (1) below:

$$I^* = \operatorname*{argmin}_{I}[\|FP(I) - Y\| + \beta R(I)], \quad (1)$$

where I* may represent an image to be reconstructed, FP may represent a forward projector, I may represent an intermediate image or intermediate image data, Y may represent the measured projection data, R(I) may represent the regularization item, and may represent the regularization parameter.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in an iteration, 610 may be unnecessary and the original image data may be determined or updated based on default settings of the processing engine 140.

Figure 7:
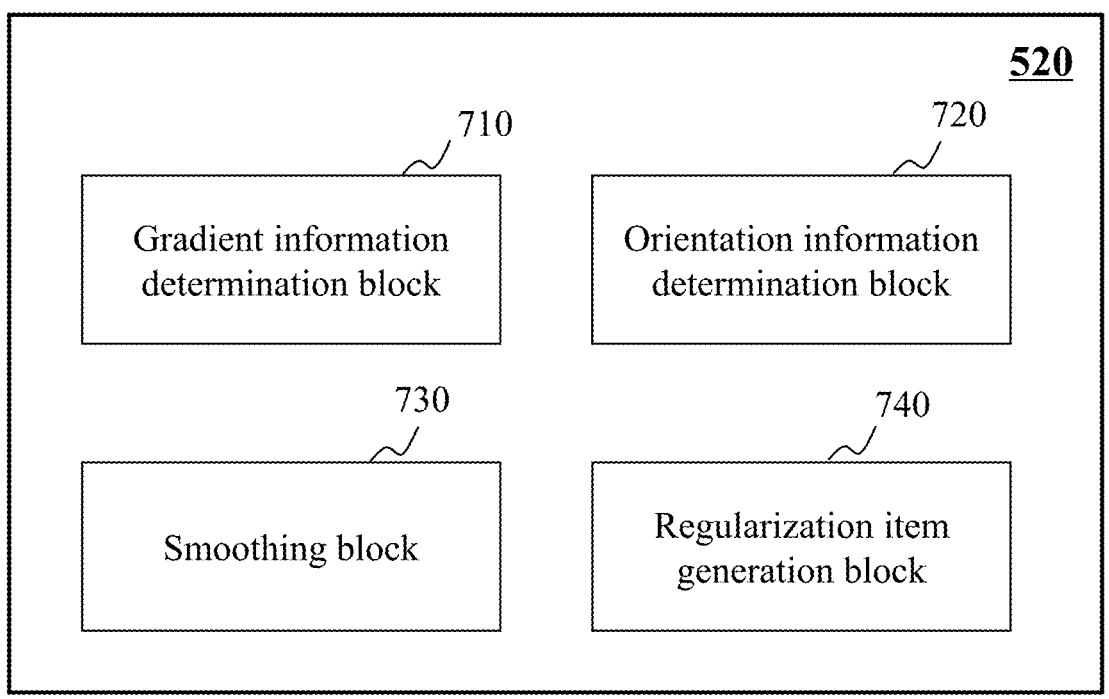
FIG. 7 is a block diagram illustrating an exemplary regularization unit according to some embodiments of the present disclosure.

FIG. 7 is a block diagram illustrating an exemplary regularization unit 520 according to some embodiments of the present disclosure. The regularization unit 520 may include a gradient information determination block 710, an orientation information determination block 720, a smoothing block 730, and a regularization item generation block 740.

The gradient information determination block 710 may determine gradient information of the image data. As used herein, the gradient information may refer to a gradient of voxel values or pixel values of the image data along a specific direction. For example, for a CT image, the gradient information may refer to a gradient of CT values of the CT image along a specific direction.

The orientation information determination block 720 may determine orientation information of the image data. As used herein, the orientation information may indicate an anisotropy of the gradient information of the image data. For example, the gradients of the image data along different directions may be different. In some embodiments, the orientation information may be associated with one or more vectors along the directions. In some embodiments, the orientation information may be expressed as a structure tensor or a matrix.

The smoothing block 730 may smooth the projection data, the image data, or the orientation information of the image data. In some embodiments, the smoothing block 730 may smooth the projection data, the image data, or the orientation information of the image data based on a filtering technique. The filtering technique may involve an amplitude limiter filter, a middle value filter, an arithmetic average filter, a recursion average filter, a first-order lag filter, a linear filter, a non-linear filter, a low-pass filter, a band-pass filter, a band-stop filter, a notch filter, a comb filter, an all-pass filter, or the like, or any combination thereof.

The regularization item generation block 740 may generate a regularization item based on the gradient information with or without the orientation information of the smoothed image data. In some embodiments, as described in connection with FIG. 6, the regularization item may be updated during the iteration process. In some embodiments, the regularization item generation block 740 may generate the regularization item based on a region of interest (ROI) of the image data. The ROI may include, for example, a liver, a kidney, a bone, a heart, a lung, a brain, a bone, or the like, or any combination thereof. It is known that the shapes and/or features of different organs of a subject may be different, and the regularization item may be used to regularize the surfaces of the organs, and therefore, different ROIs may correspond to different regularization items.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more blocks in the regularization unit 520 may each include an independent storage block (not shown). As another example, any two or more blocks may be integrated into an independent block used to implement more than one functions. As a further example, the smoothing block 730 may be omitted.

Figure 8:
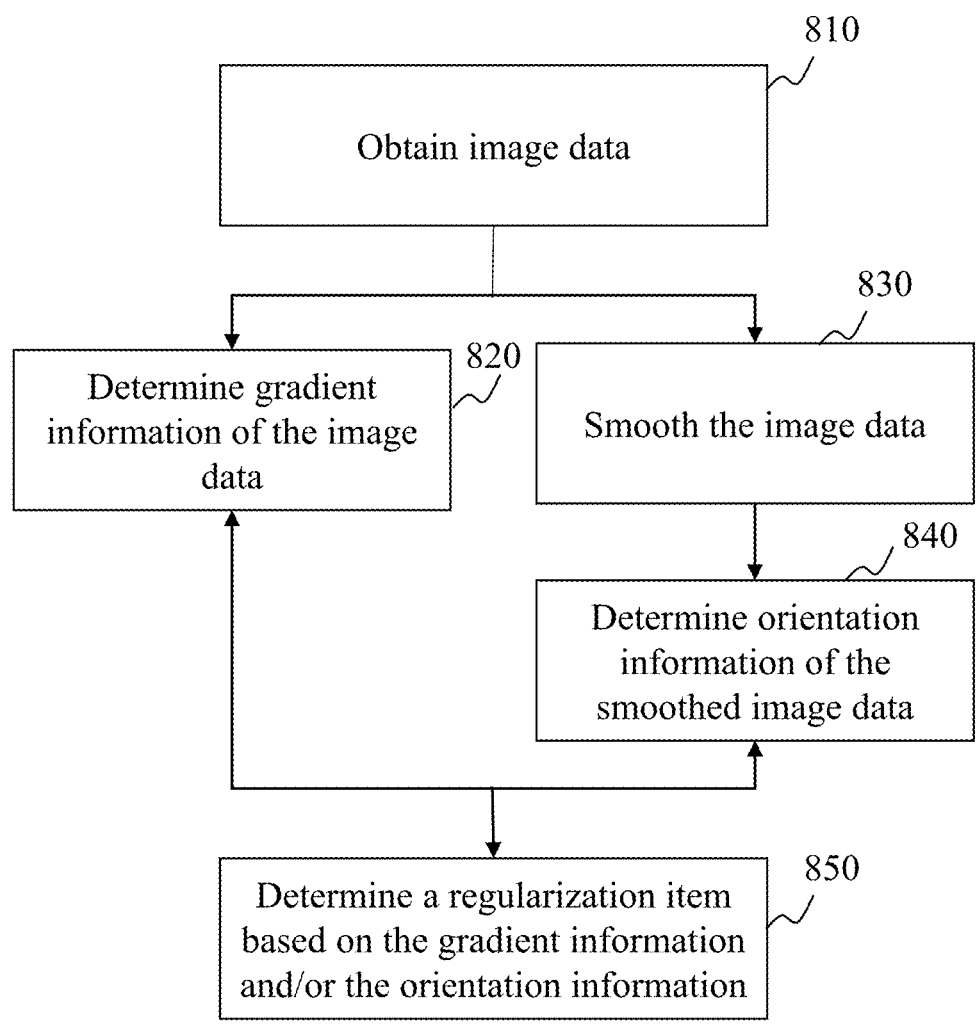
FIG. 8 is a flowchart illustrating an exemplary process for determining a regularization item according to some embodiments of the present disclosure.

FIG. 8 is a flowchart illustrating an exemplary process for determining a regularization item according to some embodiments of the present disclosure.

In 810, image data may be obtained. The image data may be obtained from the image generation unit 510.

In 820, gradient information of the image data may be determined. The gradient information of the image data may be determined by the gradient information determination block 710. For example, assuming that the image data include 2D image data, the gradient information of the image data may be determined according to formula (2) below:

$$G(i, j) = \frac{\partial I(i, j)}{\partial i} + \frac{\partial I(i, j)}{\partial j}, \quad (2)$$

where (i, j) may represent a pixel in the image data, I(i, j) may represent a value (e.g., a CT value) of the pixel in the image data, and G (i, j) may represent a first-order differentiation of the image data.

As another example, assuming that the image data include 3D image data, the gradient information of the image data may be determined according to formula (3) below:

$$G(i, j, k) = \frac{\partial I(i, j, k)}{\partial i} + \frac{\partial I(i, j, k)}{\partial j} + \frac{\partial I(i, j, k)}{\partial k}, \quad (3)$$

where (i, j, k) may represent a voxel in the image data, I(i, j, k) may represent a value (e.g., a CT value) of the voxel in the image data, and G (i, j, k) may represent a first-order differentiation of the image data.

In some embodiments, the gradient information of the image data may be expressed in the form of a matrix. The matrix may include a row matrix, a column matrix, an asymmetric matrix, a diagonal matrix, a decomposed matrix, etc. In some embodiments, the gradient information of the image data may be expressed in different coordinate systems, for example, a Cartesian coordinate system, a cylindrical coordinate system, a spherical coordinate system, etc.

In 830, the image data may be smoothed. The image data may be smoothed by the smoothing block 730. The image data may be smoothed based on a filtering technique. In some embodiments, the image data may be smoothed according to a statistical distribution of the image data. For example, in order to reduce or remove the noise(s) in the image data, the image data may be smoothed based on a first low-pass filter (e.g., a Gaussian filter) as expressed in formula (4) below:

$$I_\sigma = K_\sigma * I, \quad (4)$$

where $I_\sigma$ may represent smoothed image data, $K_\sigma$ may represent a Gaussian function, σ may represent a parameter of the Gaussian function (e.g., a standard deviation of the Gaussian function), and I may represent the image data. After the image data is smoothed, the smoothed image data may be transmitted for further processing, or stored in a storage device disclosed elsewhere in the present disclosure.

In 840, orientation information of the smoothed image data may be determined. The orientation information may be determined by the orientation information determination block 720. In some embodiments, the orientation information may indicate an anisotropy of the gradient information of the smoothed image data. For example, for a tissue in the smoothed image data, a gradient of the smoothed image data along a direction vertical to a surface of the tissue may be different from a gradient of the smoothed image data along a direction tangent to the surface of the tissue.

In 850, a regularization item may be determined based on the gradient information of the image data and/or the orientation information of the smoothed image data. For example, the regularization item may be determined according to formula (5) below:

$$R(I) = \Sigma_{\{i,j,k\} \in \Omega} \sqrt{\nabla I_{\{i,j,k\}}^T A_{\{i,j,k\}} \nabla I_{\{i,j,k\}}}, \quad (5)$$

where I may represent the image data, (i, j, k) may represent a voxel index of the image data, $\nabla I_{\{i,j,k\}}$ may represent the gradient of the voxel (i, j, k), $\nabla I_{\{i,j,k\}}^T$ may represent a transpose of the gradient of the voxel (i, j, k), Ω may represent the whole image data domain, and $A_{\{i,j,k\}}$ may represent a matrix corresponding to the orientation information of the voxel (i, j, k) in the smoothed image data.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, 830 may be omitted and the image data is not be smoothed.

Figure 9:
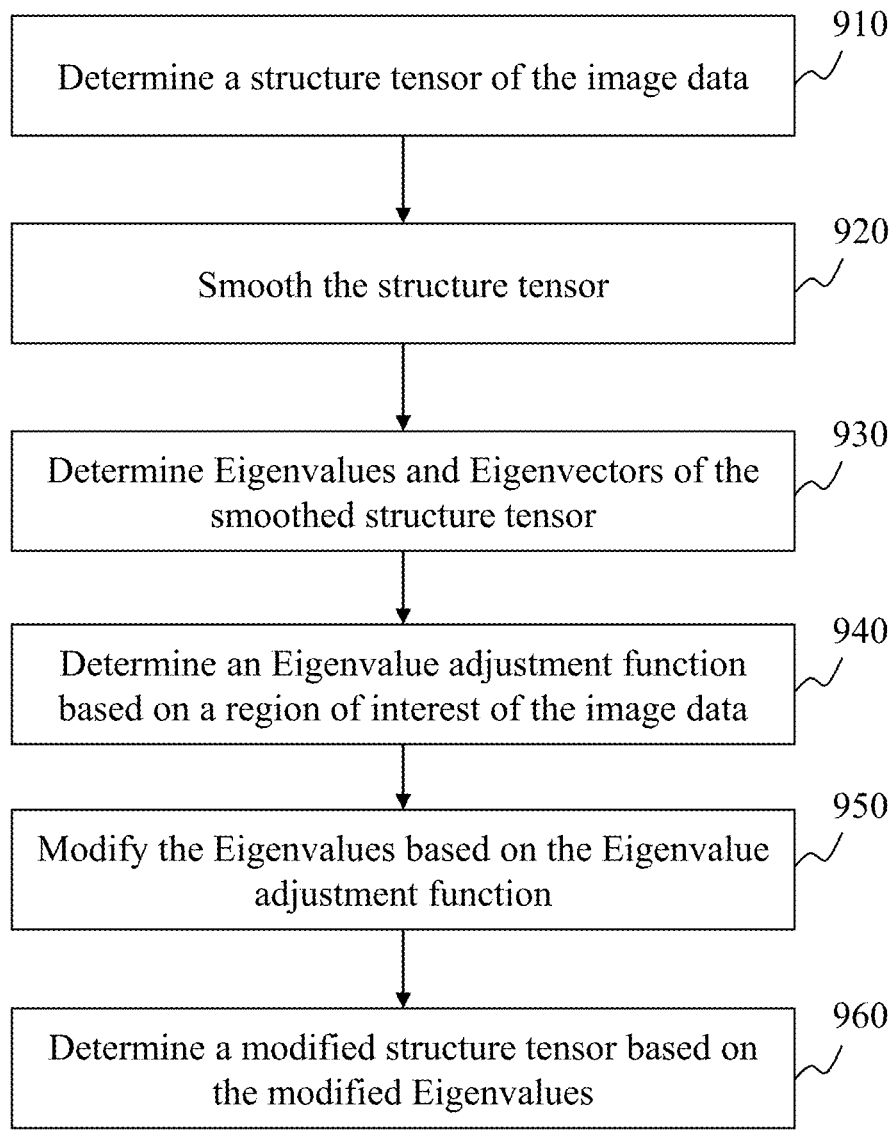
FIG. 9 is a flowchart illustrating an exemplary process for determining orientation information of image data according to some embodiments of the present disclosure.

FIG. 9 is a flowchart illustrating an exemplary process for determining orientation information of the image data or the smoothed image data according to some embodiments of the present disclosure. The process 900 may be performed by the orientation information determination block 720.

In 910, a structure tensor of the image data may be determined. In some embodiments, the structure tensor may be expressed as a matrix. For example, for 3D image data, the structure tensor may be expressed as a 3×3 matrix; and for 2D image data, the structure tensor may be expressed as a 2×2 matrix. For example, the structure tensor may be determined according to formula (6) below:

$$J = \nabla I * \nabla I^T, \quad (6)$$

where J may represent the structure tensor of the image data, I may represent the image data, ∇I may represent the gradient of the image data, $\nabla I^T$ may represent a transpose of the gradient of the image data, and * may represent a Cartesian product.

As another example, a structure tensor of the smoothed image data may be determined according to formula (7) below:

$$J' = \nabla I_\sigma * \nabla I_\sigma^T, \quad (7)$$

where J' may represent the structure tensor of the smoothed image, $I_\sigma$ may represent the smoothed image data, $\nabla I_\sigma$ may represent the gradient of the smoothed image data, and $\nabla I_\sigma^T$ may represent the transpose of the gradient of the smoothed image data.

In 920, the structure tensor may be smoothed. For example, the structure tensor may be smoothed based on a second low-pass filter (e.g., a Gaussian filter) according to formula (8) below:

$$J_\rho = K_\rho * J', \quad (8)$$

where $J_\rho$ may represent the smoothed structure tensor, $K_\rho$ may represent a Gaussian function, J' may represent the structure tensor of the smoothed image data, ρ may represent a parameter of the Gaussian function (e.g., a standard deviation of the Gaussian function), and the asterisk * may represent a Cartesian product. It should be noted that in this disclosure it takes image data of an image as a whole to describe a process (e.g., the process 800, the process 900, etc.); however, an image may be actually processed on the voxel level. For example, a specific voxel in the image data may correspond to a specific structure tensor in the form of, for example, a 3×3 matrix. The Gaussian function may be applied to each component of the 3×3 matrix based on a plurality of smoothed structure tensors corresponding to a plurality of neighboring voxels. As used herein, a neighboring voxel of a subject voxel may refer to a voxel that is within a certain distance from the subject voxel. For instance, a neighboring voxel of a subject voxel may refer to a voxel that is one voxel, two voxels, three voxels, etc., away from the subject voxel. The distance may be assessed along a direction, e.g., along a horizontal direction, along a vertical direction, or along a diagonal direction.

In 930, Eigenvalues of the smoothed structure tensor may be determined. The Eigenvalues may be determined by decomposing the smoothed structure tensor based on an Eigenvalue decomposition approach. For example, for 3D image data, the structure tensor or the smoothed structure tensor may be decomposed as three Eigenvalues and three Eigenvectors according to formula (9) below:

$$J_\rho = [\underline{v}_1 \; \underline{v}_2 \; \underline{v}_3] \begin{bmatrix} u_1 & & \\ & u_2 & \\ & & u_3 \end{bmatrix} \begin{bmatrix} \underline{v}_1^T \\ \underline{v}_2^T \\ \underline{v}_3^T \end{bmatrix}, \quad (9)$$

where $J_\rho$ may represent the smoothed structure tensor, $\underline{v}_1$, $\underline{v}_2$, and $\underline{v}_3$ may represent the Eigenvectors of the smoothed structure tensor, $\underline{v}_1^T$, $\underline{v}_2^T$, and $\underline{v}_3^T$ may represent transposes of the three Eigenvectors respectively, and $u_1$, $u_2$, and $u_3$ may represent the Eigenvalues of the smoothed structure tensor.

In 940, an Eigenvalue adjustment function may be determined based on a region of interest (ROI). The ROI may include a liver, a kidney, a bone, a heart, a lung, a brain, a bone, or the like, or any combination thereof. It is known that different ROIs may correspond to different tissues or organs of a subject, and that for different tissues or organs, surfaces may be different. For a specific tissue or organ, in order to enhance the surface (i.e., edge) of the tissue or organ, a specific Eigenvalue adjustment function may be determined. Different Eigenvalue adjustment functions may achieve different edge enhancing effects. For example, an Eigenvalue adjustment function may be determined as formula (10) below:

$$f(\eta_1, \eta_2, \eta_3; u_1, u_k) = \qquad\qquad\qquad (10)$$
$$\eta_1 + (1 - \eta_1)\exp\left(-\frac{\eta_2}{(u_k - u_1)^2}\right)\left(1 - \exp\left(-\frac{\eta_2}{(u_k - u_1)^2}\right)\right)^{\eta_3},$$

where $f(\eta_1, \eta_2, \eta_3; u_1, u_k)$ may represent the Eigenvalue adjustment function, $\eta_1$, $\eta_2$, and $\eta_3$ may be predetermined parameters, and $u_k$ may be $u_2$ or $u_3$. As used herein, $\eta_1$ may be used to define a scale of the Eigenvalues, $\eta_2$ and $\eta_3$ may be used to determine where the peak of a characteristic curve of the Eigenvalue adjustment function (e.g., the characteristic curves illustrated in FIG. 10) will be and how quickly the characteristic curve decreases to 0.

As another example, an Eigenvalue adjustment function may be determined as formula (11) below $$f_{sin}(\eta_0, \eta_1, \eta_2, \eta_3, du) = \qquad\qquad (11)$$
$$\begin{cases} \eta_1 & du \in [0, \eta_0) \\ \eta_1 + (1-\eta_1)\sin\frac{\pi(du-\eta_0)}{2(\eta_2-\eta_0)} & du \in [\eta_0, \eta_2) \\ \eta_1 + (1-\eta_1)\sin\frac{\pi\eta_3^2}{2((du-\eta_2)^2+\eta_3^2)} & du \in [\eta_2, +\infty) \end{cases},$$

where $du$ may be $(u_2-u_1)$ or $(u_3-u_1)$.

As a further example, an Eigenvalue adjustment function may be determined as formula (12) below:

$$f(\eta_1, \eta_2, \eta_3, \eta_4; u_1, u_k) = \qquad\qquad (12)$$
$$1 - (1-\eta_1)\exp\left(-\frac{\eta_2}{(u_k-u_1)^{\eta_4}}\right)\left(1 - \exp\left(-\frac{\eta_2}{(u_k-u_1)^{\eta_4}}\right)\right)^{\eta_3},$$

where $\eta_4$ may be a predetermined parameter.

As a still further example, an Eigenvalue adjustment function may be determined as formula (13) below:

$$f(\eta_1, \eta_2, \eta_3, \eta_4; u_1, u_k) = 1 - (1-\eta_1)\exp\left(-\frac{\eta_2}{u_k^{\eta_4}}\right)\left(1 - \exp\left(-\frac{\eta_2}{u_k^{\eta_4}}\right)\right)^{\eta_3}. \quad (13)$$

As a still further example, an Eigenvalue adjustment function may be determined as formula (14) below:

$$f(\eta_1, \eta_2, \eta_3, \eta_4; u_1, u_k) = 1 - (1-\eta_1)\exp\left(-\frac{\eta_2}{u_d^{\eta_4}}\right)\left(1 - \exp\left(-\frac{\eta_2}{u_d^{\eta_4}}\right)\right)^{\eta_3}, \quad (14)$$

where $u_d$ may be a predefined value.

As a still further example, an Eigenvalue adjustment function may be determined as formula (15) below:

$$f(\eta_1, \eta_2, \eta_3, \eta_4; u_1, u_k) = \qquad\qquad (15)$$
$$\eta_1 + (1-\eta_1)\exp\left(-\frac{\eta_2}{(u_d-u_k)^{\eta_4}}\right)\left(1 - \exp\left(-\frac{\eta_2}{(u_d-u_k)^{\eta_4}}\right)\right)^{\eta_3}.$$

As a still further example, an Eigenvalue adjustment function may be determined as formula (16) below:

$$f(\eta_1, \eta_2, \eta_3, \eta_4; u_1, u_k) = \qquad\qquad (16)$$
$$\eta_1 + (1-\eta_1)\exp\left(-\frac{(u_k+\eta_2)^{\eta_4}}{(u_d-u_k)^{\eta_4}}\right)\left(1 - \exp\left(-\frac{(u_k+\eta_2)^{\eta_4}}{(u_d-u_k)^{\eta_4}}\right)\right)^{\eta_3}.$$

In 950, the Eigenvalue may be modified based on the Eigenvalue adjustment function(s). For example, the modified Eigenvalue may be determined according to formula (17), formula (18), and formula (19) below:

$$\lambda_1 = \eta_1 \in (0,1], \qquad\qquad (17)$$

$$\lambda_2 = f(\eta_1, \eta_2, \eta_3; u_1, u_2), \qquad\qquad (18)$$

$$\lambda_3 = f(\eta_1, \eta_2, \eta_3; u_1, u_3), \qquad\qquad (19)$$

where $\lambda_1$, $\lambda_2$, and $\lambda_3$ may represent the modified Eigenvalues. In some embodiments, the modified Eigenvalue may be determined based on different Eigenvalue adjustment functions determined in 940.

In 960, a modified structure tensor may be determined based on the modified Eigenvalue. For example, the modified structure tensor may be determined according to formula (20) below:

$$A = [\underline{v}_1\ \underline{v}_2\ \underline{v}_3] \begin{bmatrix} \lambda_1 & & \\ & \lambda_2 & \\ & & \lambda_3 \end{bmatrix} \begin{bmatrix} \underline{v}_1^T \\ \underline{v}_2^T \\ \underline{v}_3^T \end{bmatrix}, \quad (20)$$

where A may represent the modified structure tensor, $\lambda_1$, $\lambda_2$, and $\lambda_3$ may represent the modified Eigenvalues, respectively.

Further, as described in connection with 960, a regularization item may be determined based on the modified structure tensor based on, for example, formula (5).

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, 920 may be unnecessary.

Figure 10:
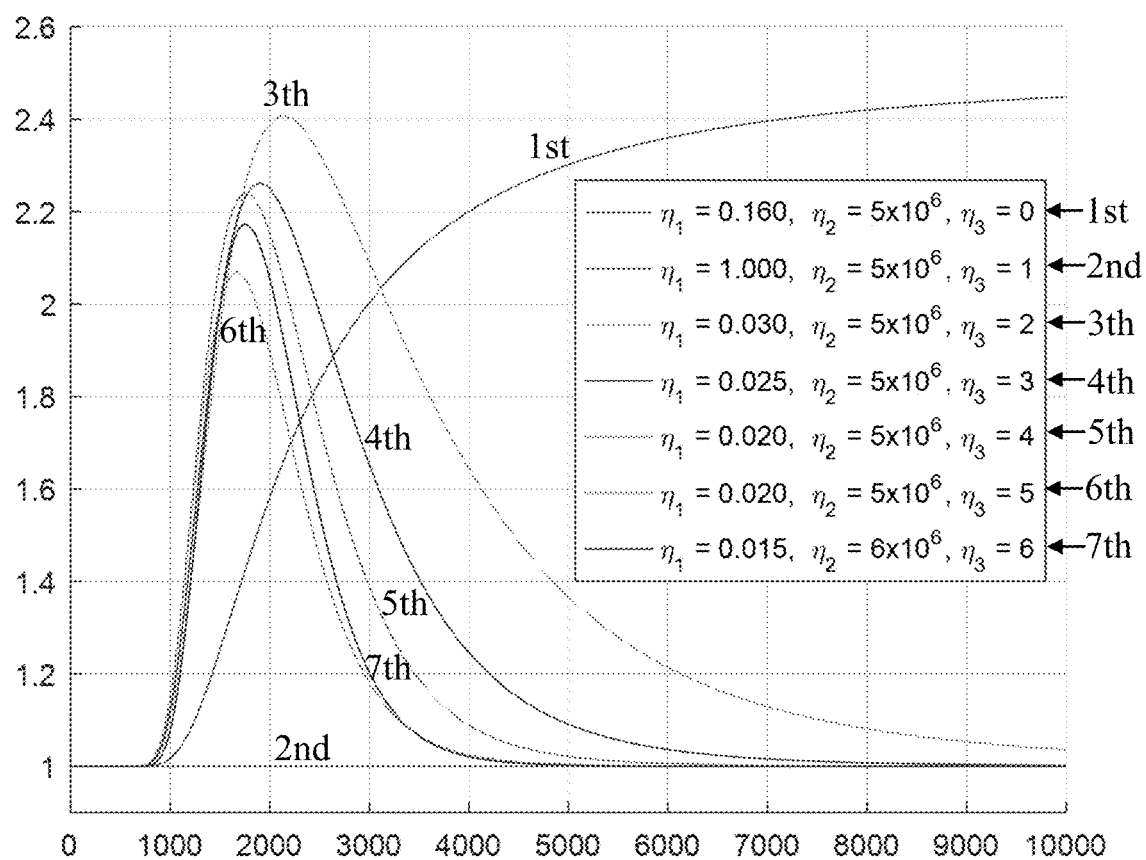
FIG. 10 illustrates exemplary characteristic curves of an Eigenvalue adjustment function according to some embodiments of the present disclosure.

FIG. 10 illustrates exemplary characteristic curves of an Eigenvalue adjustment function according to some embodiments of the present disclosure. For illustration purposes, the characteristic curves were determined based on the Eigenvalue adjustment function expressed as formula (10). As shown in FIG. 10, the horizontal coordinate may represent $(u_k-u_1)^2$ illustrated in formula (10), and the vertical coordinate may represent possible values (i.e., possible values of the Eigenvalues) of the Eigenvalue adjustment function. As used herein, $(u_k-u_1)^2$ may refer to the square of a difference between a first gradient of the image data along a direction $\underline{v}_k$ and a second gradient of the image data along a direction $\underline{v}_1$. The larger the square of the difference, the more clear the edge of a tissue or organ may be. Take the sixth characteristic curve as an example, it may be seen that the square of the difference approximates 2000, that is, the difference between the first gradient and the second gradient approximates 45. In this situation, the edge of a soft tissue (e.g., a liver) may be suitable.

EXAMPLES

The following example is provided for illustration purposes, and not intended to limit the scope of the present disclosure.

Example 1

FIG. 11-A and FIG. 11-B illustrate exemplary CT images reconstructed based on different reconstruction approaches according to some embodiments of the present disclosure. The CT image illustrated in FIG. 11-A was reconstructed based on a total variation approach, and the CT image illustrated in FIG. 11-B was reconstructed based on the regularization item that was determined based on a structure tensor (e.g., a structure tensor modified according to formula (11)) disclosed in this disclosure. As illustrated in FIG. 11-A, the right side is an enlarged view of a region marked with $M_1$ in the left side; similarly, in FIG. 11-B, the right side is an enlarged view of a region marked with $M_2$ in the left side. It may be seen that an edge of a liver (e.g., a region marked with $N_2$) illustrated in FIG. 11-B is smoother than that (e.g., a region marked with $N_1$) illustrated in FIG. 11-A.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An image reconstruction method implemented on at least one machine each of which has at least one processor and at least one storage device, the method comprising:
   obtaining image data, at least a portion of the image data relating to a region of interest (ROI);
   smoothing the image data;
   determining a structure tensor based on the smoothed image data;
   smoothing the structure tensor;
   determining eigenvalues of the smoothed structure tensor;
   modifying the eigenvalues of the smoothed structure tensor based on an eigenvalue adjustment function, wherein a peak value of a characteristic curve and a slope of the characteristic curve are adjusted to determine one or more parameters of the eigenvalue adjustment function;
   determining a modified structure tensor based on the modified eigenvalues; and
   generating an image based on the modified structure tensor.

2. The method of claim 1, wherein the ROI comprising a region relating to a liver, a bone, or a kidney.

3. The method of claim 1, wherein the characteristic curve indicates a relationship between a possible eigenvalue and gradient information of the image data modifying.

4. The method of claim 1, wherein the eigenvalue adjustment function includes a factor of a scale of the eigenvalues.

5. The method of claim 1, wherein the smoothing the image data comprising smoothing the image data based on a first low-pass filter.

6. The method of claim 1, wherein the determining a structure tensor based on the smoothed image data comprising:
   determining a first-order differentiation of the smoothed image data;
   determining a transpose of the first-order differentiation of the smoothed image data; and
   determining the structure tensor based on the first-order differentiation of the smoothed image data and the transpose of the first-order differentiation of the smoothed image data.

7. The method of claim 1, wherein the smoothing the structure tensor comprising applying a second low-pass filter on the structure tensor.

8. The method of claim 1, wherein the obtaining image data comprising:
   obtaining projection data; and
   generating the image data based on the projection data.

9. The method of claim 1, wherein the image data comprising a 2D image, 2D image data, a 3D image, or 3D image data.

10. The method of claim 1, wherein the generating the image data based on the projection data comprising updating the image data based on an iterative statistical reconstruction algorithm.

11. A system, comprising:

at least one processor, and a storage device for storing instructions that, when executed by the at least one processor, the system is configured to effectuate operations comprising:

obtaining image data, at least a portion of the image data relating to a region of interest (ROI);

smoothing the image data;

determining a structure tensor based on the smoothed image data;

smoothing the structure tensor;

determining eigenvalues of the smoothed structure tensor;

modifying the eigenvalues of the smoothed structure tensor based on an eigenvalue adjustment function, wherein a peak value of a characteristic curve and a slope of the characteristic curve are adjusted to determine one or more parameters of the eigenvalue adjustment function;

determining a modified structure tensor based on the modified eigenvalues; and generating an image based on the modified structure tensor.

12. The system of claim 11, wherein the ROI comprising a region relating to a liver, a bone, or a kidney.

13. The system of claim 11, wherein the characteristic curve indicates a relationship between a possible eigenvalue and gradient information of the image data.

14. The system of claim 11, wherein the eigenvalue adjustment function includes a factor of a scale of the eigenvalues.

15. The system of claim 11, wherein the smoothing the image data comprising smoothing the image data based on a first low-pass filter.

16. The system of claim 11, wherein the determining a structure tensor of the smoothed image data comprising:

determining a first-order differentiation of the smoothed image data;

determining a transpose of the first-order differentiation of the smoothed image data; and determining the structure tensor based on the first-order differentiation of the smoothed image data and the transpose of the first-order differentiation of the smoothed image data.

17. The system of claim 11, wherein the smoothing the structure tensor comprising applying a second low-pass filter on the structure tensor.

18. The system of claim 11, wherein the obtaining image data comprising:

obtaining projection data; and generating the image data based on the projection data.

19. The system of claim 11, wherein the image data comprising a 2D image, 2D image data, a 3D image, or 3D image data.

20. A non-transitory computer readable medium comprising executable instructions that, when executed by at least one processor, cause the at least one processor to effectuate a method for image reconstruction, the method comprising:

obtaining image data, at least a portion of the image data relating to a region of interest (ROI);

smoothing the image data;

determining a structure tensor of the smoothed image data;

smoothing the structure tensor;

determining eigenvalues of the smoothed structure tensor;

modifying the eigenvalues of the smoothed structure tensor based on an eigenvalue adjustment function, wherein a peak value of a characteristic curve and a slope of the characteristic curve are adjusted to determine one or more parameters of the eigenvalue adjustment function;

determining a modified structure tensor based on the modified eigenvalues; and generating an image based on the modified structure tensor.

* * * * *